(12) United States Patent
Kyle et al.

(10) Patent No.: US 8,577,446 B2
(45) Date of Patent: Nov. 5, 2013

(54) STRESS DETECTION DEVICE AND METHODS OF USE THEREOF

(76) Inventors: Bobby Kyle, Danielsville, GA (US); Vardis Benson, Braselton, GA (US); Gabe Abreo, Kansas City, MO (US)

( * ) Notice: Subject to any disclaimer, the term of this patent is extended or adjusted under 35 U.S.C. 154(b) by 981 days.

(21) Appl. No.: 11/934,868

(22) Filed: Nov. 5, 2007

(65) Prior Publication Data

US 2011/0040191 A1 Feb. 17, 2011

Related U.S. Application Data (60) Provisional application No. 60/864,420, filed on Nov. 6, 2006, provisional application No. 60/952,997, filed on Jul. 31, 2007.

(51) Int. Cl.
*A61B 6/00* (2006.01)

(52) U.S. Cl.
USPC ........... 600/473; 600/372; 600/382; 600/476; 600/558; 348/164; 348/207.99

(58) Field of Classification Search
USPC .......... 600/372, 382, 558, 473, 476; 340/5.81
See application file for complete search history.

(56) References Cited

U.S. PATENT DOCUMENTS

| | | | |
|---|---|---|---|
| 5,406,956 A | 4/1995 | Farwell | |
| 5,507,291 A | 4/1996 | Stirbl et al. | |
| 5,720,298 A | 2/1998 | Papakostopoulos | |
| 5,771,261 A | 6/1998 | Anbar | |
| 5,876,334 A | 3/1999 | Levy | |
| 6,023,637 A | 2/2000 | Liu et al. | |
| 6,656,116 B2 | 12/2003 | Kim et al. | |
| 6,754,524 B2 | 6/2004 | Johnson | |
| 6,837,615 B2 | 1/2005 | Newman | |
| 6,854,879 B2 | 2/2005 | Pavlidis | |
| 6,996,256 B2 | 2/2006 | Pavlidis | |
| 7,027,621 B1 | 4/2006 | Prokoski | |
| 7,085,420 B2 * | 8/2006 | Mehrotra | 382/232 |
| 7,111,980 B2 | 9/2006 | Pavlidis et al. | |
| 7,138,905 B2 * | 11/2006 | Pavlidis et al. | 340/5.81 |
| 7,488,294 B2 * | 2/2009 | Torch | 600/558 |
| 7,887,533 B2 * | 2/2011 | Barolet et al. | 606/9 |
| 2002/0058867 A1 | 5/2002 | Breiter et al. | |
| 2003/0012253 A1 | 1/2003 | Pavlidis | |
| 2003/0016726 A1 | 1/2003 | Pavlidis | |
| 2003/0120140 A1 | 6/2003 | Bango | |
| 2003/0179807 A1 | 9/2003 | Newman | |
| 2004/0225222 A1 | 11/2004 | Zeng et al. | |
| 2004/0249258 A1 | 12/2004 | Tupin et al. | |

(Continued)

FOREIGN PATENT DOCUMENTS

WO 9808431 3/1998

OTHER PUBLICATIONS

Pavlidis; Levine J.; "Monitoring of Periorbital Blood Flow Rate Through Thermal Image Analysis and Its Application to Polygraph Testing", Oct. 25-28, 2001, Proceeding of the 23rd Annual International Conference of the IEEE Engineering in Medicine and Biology Society, Istanbul, Turkey.

(Continued)

*Primary Examiner* — Baisakhi Roy
(74) *Attorney, Agent, or Firm* — Rodgers & Rodgers (57) ABSTRACT

Described herein are stress detection systems and methods of using such systems.

7 Claims, 6 Drawing Sheets

(56) References Cited

U.S. PATENT DOCUMENTS

2004/0254472 A1    12/2004   McQuilkin
2005/0054935 A1    3/2005   Rice et al.
2007/0177017 A1*   8/2007   Kyle et al. ................ 348/207.99

OTHER PUBLICATIONS

Pavlidis, Ioannis; Eberhardt, Norman L.; Levine, James A., "Seeing through the face of deception", Nature, vol. 415, pp. 35, Jan. 2002.

* cited by examiner

| Color | Hex Value | Decimal Value |
|---|---|---|
| Black | 0x00000000 | 0 |
| Red | 0x000000FF | 256 |
| White | 0x00FFFFFF | 16777215. |
| Blue | 0x00FF0000 | 16711680. |
| Yellow | 0X0000FFFF | 65535. |

STRESS DETECTION DEVICE AND METHODS OF USE THEREOF

CROSS REFERENCE TO RELATED APPLICATIONS

This application claims priority upon U.S. provisional application Ser. Nos. 60/864,420, filed Nov. 6, 2006; and 60/952,997, filed Jul. 31, 2007. These applications are hereby incorporated by reference in their entireties for all of their teachings.

BACKGROUND

The detection of stress has numerous applications in the security field. For example, in airports, it would be desirable to measure or detect stress of individuals that have been singled out and will be interviewed. Military applications include interviewing suspected terrorists in fixed facilities and in remote locations. In other instances, stress can be an indication of untruthfulness. Thus, for example, the detection of stress can be useful during police interrogations as an indicator of untruthfulness. In addition, the detection of stress can be used by parole boards to help determine stress levels when addressing certain topics that would be sensitive to the reason for the incarceration of the individual. The detection of stress in the corporate world can be useful when interviewing personal for sensitive job positions in high security applications.

In general, the detection of stress in a subject involves invasive techniques, where a device needs to be physically attached to the subject. With security applications, invasive techniques are impractical and offer little value. Thus, it would be desirable to detect stress levels in a subject without the subject knowing he is being examined. One approach is to measure the skin temperature of the subject. U.S. Pat. No. 5,771,261 to Anbar describes how dynamic area telethermometry (DAT) can be used to detect changes in skin temperature and skin perfusion and subsequently correlate the changes to mental stress. Thus, the use of infrared cameras to measure changes in a subject's skin temperature during police interrogations can be an indication of whether or not the subject is being honest when responding to questions.

Although the use of infrared cameras provides useful information about the stress level of a subject, the results in the absence of other data can be misleading. For example, changes in temperature in a police interrogation room may result in an increase in skin temperature. Further, prolonged interrogations can also provide a steady increase in skin temperature. Thus, what is needed is a device that can simultaneously measure or detect a plurality of stress indicators in a subject. For example, by simultaneously measuring or detecting changes in several features of the subject, it is possible to more reliably determine whether or not the subject is being truthful. Described herein are stress detection devices and methods of using thereof that overcome the limitations of previous stress detection devices.

BRIEF DESCRIPTION OF THE DRAWINGS

The accompanying drawings, which are incorporated in and constitute a part of this specification, illustrate several aspects described below. It will be appreciated that these drawings depict only typical embodiments of the materials, articles, and methods described herein and are therefore not to be considered limiting of their scope.

DESCRIPTION

Figure 1:
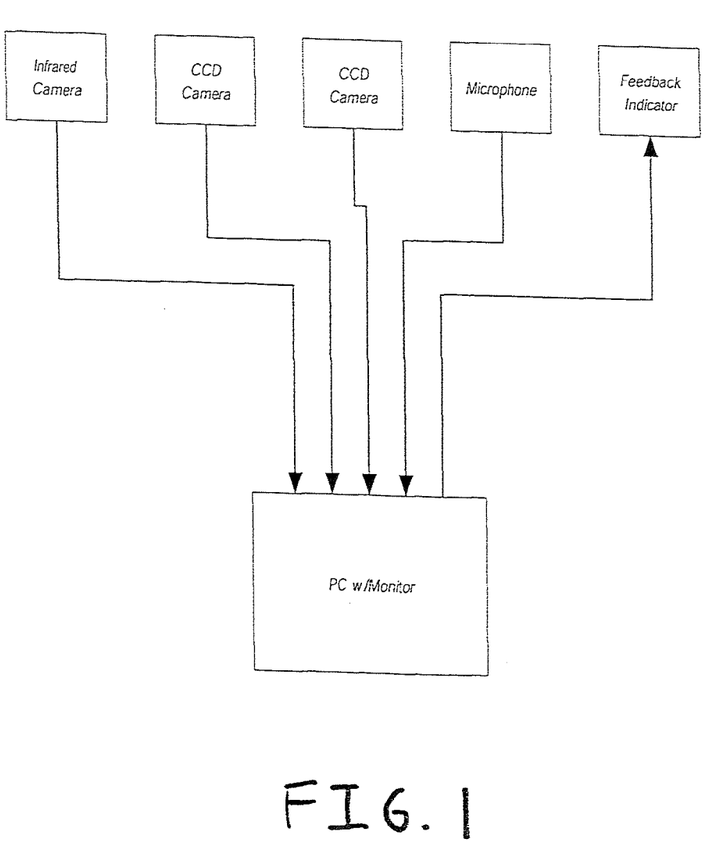
FIG. 1 is a block diagram of a computer-based system for detecting stress.

In the exemplary embodiment of the invention illustrated in FIG. 1, a system for detecting stress in a subject (person) comprises a computer system, one or more visible-light video cameras, one or more infrared video cameras, and a microphone. As described in further detail below, the system is used to measure stress experienced by a subject, such as a person being interviewed, based on an analysis of a combination of the visible-light video and infrared video of the subject. The system can further include a feedback indicator for providing feedback to the interviewer, as described in further detail below.

The computer system can comprise, for example, a desktop or laptop personal computer (PC) with associated keyboard, monitor, mouse, etc. (not shown for purposes of clarity). The computer system includes a suitable graphics card or similar device that performs analog-to-digital conversion to capture the video from the cameras. The computer system operates in accordance with suitable software programming to affect the methods described below.

The infrared camera or other thermal imager detects changes in skin temperature of the subject by continuously monitoring the modulation (i.e., increase or decrease) of skin temperature. The mechanism by which infrared cameras can measure skin temperature caused by stress is well-understood in the art and therefore not described in further detail herein. (See, e.g., U.S. Pat. No. 5,771,261 to Anbar.) It is contemplated that the infrared camera can detect all ranges of infrared energy emitted from the subject, including near infrared (0.7 µm to 1.4 µm), short-wave infrared (1.4 µm to 3 µm), mid-wave infrared (3 µm to 8 µm), long-wave infrared (8 µm to 15 µm), far infrared (15 µm to 1,000 µm), and any combination thereof. It is also contemplated that two or more thermal imagers can be used. For example, one infrared camera can be used to measure long-wave infrared energy while a second infrared camera can be used to measure mid-wave infrared energy. The term "detect" as used herein involves qualitative changes in skin temperature. Quantitative changes in skin temperature can be measured, which will be discussed below. The infrared camera produces analog and/or digital representations of the subject, which is subsequently converted to video output data. This will be discussed in greater detail below. Any suitable infrared camera can be used herein. In one aspect, infrared cameras such as, for example, ISG K6800, FLIR P60, and Macron 7604P can be used herein.

Figure 6:
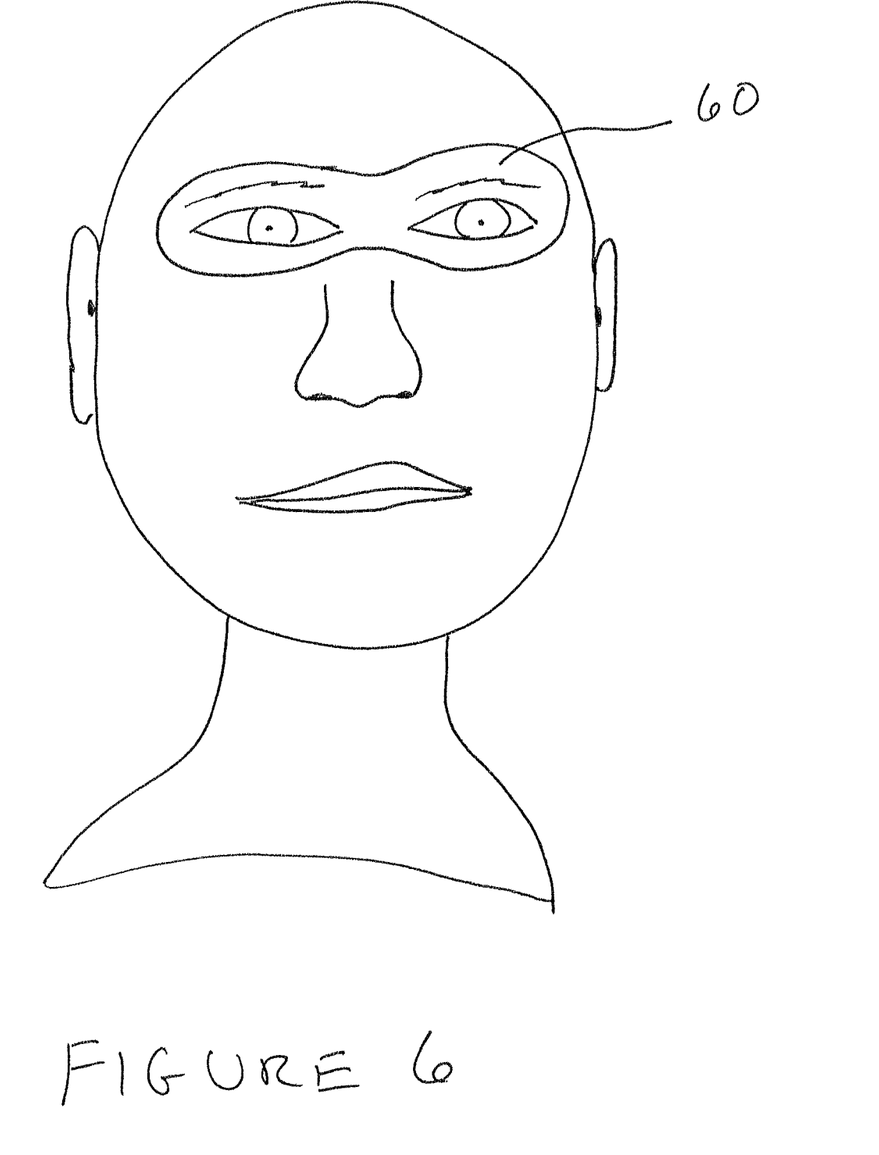
FIG. 6 shows the periorbital region of a subject.

In certain aspects, the infrared camera can detect changes in skin temperature where the skin of the subject is exposed. In one aspect, the changes in skin temperature are detected at the face, including the ears, cheeks, neck, and forehead. In other aspects, when changes in facial skin temperature can be detected, the periorbital region of the subject is excluded. The periorbital region of a subject is shown in FIG. 6 as region 60.

The periorbital region does not include the cheeks or forehead of the subject, but includes the eyes, eyelids, caruncle, and muscles surrounding the eyes where blood flow occurs with subsequent changes in skin temperature. The periorbital region is generally the hottest portion of the face.

In this aspect, the thermal imager's level and span is adjusted such that the periorbital region falls beyond the thermal camera's saturation point. For example, the gain, offset, level, and span of the thermal imager can be adjusted to optimize the imager's dynamic range such that the imager is able to resolve only the data in the areas of interest. In the case of the periorbital region, which is the hottest part of the face, the imager can be adjusted such that the temperature of the periorbital region falls outside the limits of a thermal imager. Software embedded in the thermal imager can be used to accomplish this. Thus, any imagery from the periorbital region is overexposed or "saturated." This results in no useful temperature data from this region, while the imager is still able to resolve temperature data from the other cooler parts of the face. For example, the imager can be adjusted to measure temperature changes at the second hottest part of the face (e.g., the cheeks) and set the imager such that the temperature of this area falls just below the saturation point while ensuring that temperature changes associated with the periorbital region fall above the saturation point. Thus, thermal data from the subject's periorbital region of the face is irresolvable with no return or display of detectable changes in thermal data from the periorbital region. However, thermal data from other areas of the subject's face (e.g., cheeks, ears, forehead, and neck) are available for observation by the system's operator.

In certain aspects, it is desirable to exclude thermal data from the periorbital region, as this data can be misleading at times to an examiner for detecting stress. This is due in part to the fact that as discussed above, the periorbital region is the hottest part of the face. When a subject experiences increased levels of stress, the most significant and visible temperature changes occur outside the central periorbital region (e.g., the cheeks, forehead, temple regions, and the upper neck). Areas with the largest degree of temperature change will be the most dynamic, most effective, and most reliable areas to track when detecting stress levels in a subject. In the case of the periorbital region, the changes in temperature are not as pronounced due to the fact the periorbital region is the hottest part of the face. Thus, excluding the periorbital regions in certain aspects can provide more reliable information with regards to detecting changing stress levels in a subject.

In certain aspects, it may be desirable to quantify the change in skin temperature as a measure of stress in a subject. In one aspect, the device further comprises a means for detecting statistically significant changes in periodic modulation of skin temperature of the subject. In one aspect, the computer system can operate in accordance with software that affects a cluster analysis process to measure statistically significant changes in skin temperature. The cluster analysis disclosed in U.S. Pat. No. 5,771,261 to Anbar, which is incorporated by reference, can be used herein. In cluster analysis, which is well known in the art, each frequency-amplitude pair of a fast Fourier transform (FFT) spectrum generated by the thermal imager (e.g., infrared camera) is represented by a dot on a plane that is described by amplitude versus frequency coordinates. Different FFT spectrum generated by the thermal imager are represented by a different clusters on the same plane. The two clusters may partially overlap, and a mathematical procedure, well known in the art, can determine the level of significance of the difference between the two spectra, represented by the extent of overlap of the two clusters. A common measure of the difference between two clusters is the calculated probability (p) that the two clusters compared are actually members of a single cluster, i.e., that statistically there is no difference between those two clusters. It is generally accepted that if p is smaller than 0.05 (i.e., that there is less than a 5% chance that the two clusters are identical) the difference between the two clusters is statistically significant. In another aspect, the stress detection device does not measure quantitatively changes in skin temperature such as, for example, statistically significant changes in skin temperature described above.

The visible-light video cameras are used to capture corresponding video images of the subject during questioning. In one aspect, the video camera comprises at least one CCD camera. In another aspect, the video camera comprises two CCD cameras. The number and types of cameras that can be used will vary depending upon the application and location of the device (e.g., portable vs. fixed systems). In certain aspects, the visible-light video camera that is used can cover a narrow field of vision that is aligned at the same angle as that of the thermal imager (e.g., infrared camera). In this aspect, the visible-light video camera is focused on the face of the subject. In other aspects, the visible-light video camera can be a wide field of vision camera that can be used to film the entire body of the subject or the upper torso of the subject. It is contemplated that one or more narrow and wide field of view cameras can be used and aligned at various angles with respect to the subject to provide as much visual information as needed about the subject during questioning.

The graphics card of the computer system receives video signals from the infrared and visible-light cameras and audio signals from the microphone and produces digital representations of the subject and subject's voice that can be viewed on the computer screen (or listened to, in the case of voice), recorded on disk or other medium, transmitted to a remote location, and manipulated in any other suitable manner under control of software operating on the computer system. The software can provide several display modes through which a user can choose to simultaneously display a single image, two (dual) images (e.g., side-by-side on the screen), three images, four (quad) images, etc. The images can include any suitable combination of the infrared and visible camera video. Thus, one or more infrared video images can be displayed on the screen simultaneously with one or more visible-light video images. Viewing an infrared video image simultaneously with a corresponding visible-light video image of the subject and while simultaneously listening to the interviewer's voice (questions) helps an investigator assess whether observed temperature changes are more likely due to stress than environmental or other factors.

Figure 2:
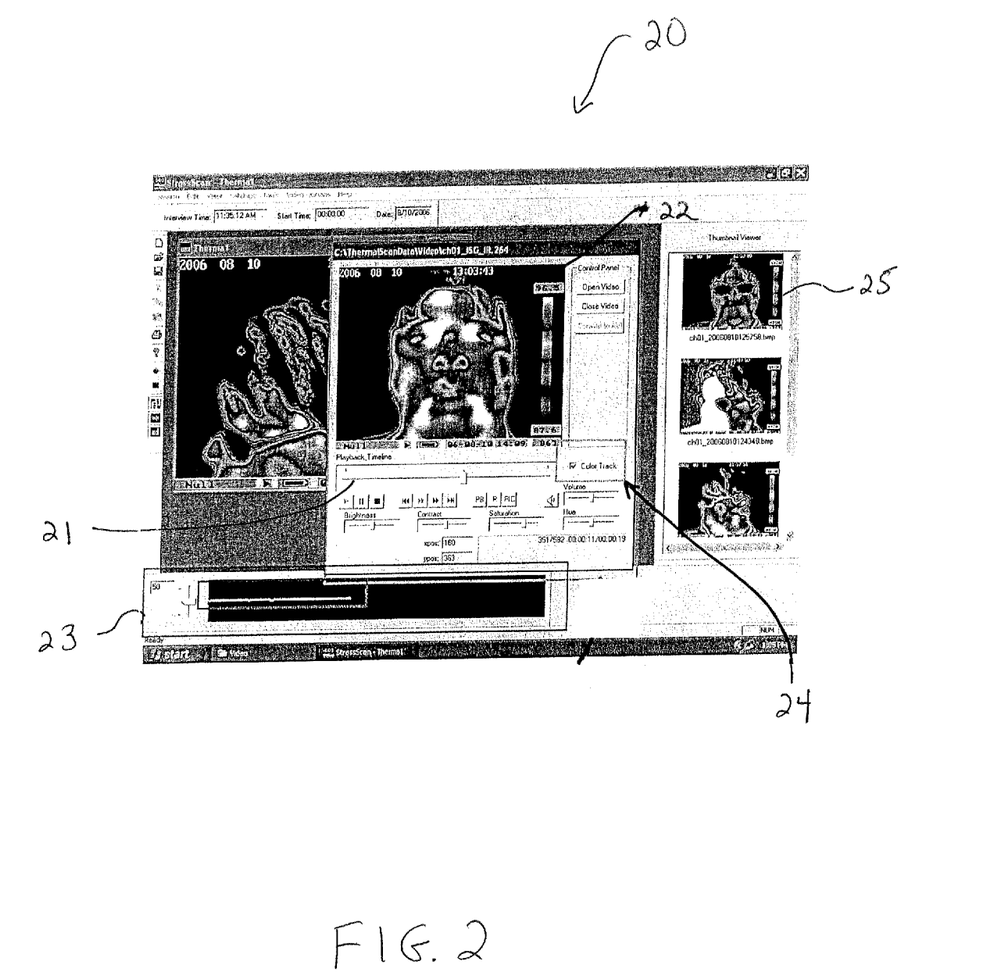
FIG. 2 depicts an exemplary screen display generated by computer software operating on the computer of FIG. 1.

As illustrated in FIG. 2, the software provides a graphical user interface (GUI) 20 through which the user (investigator) can view recorded images and representations of recorded voice. The GUI includes a playback module or window that displays the recorded video. A "Timeline" slider control 21 allows the user to select the point in the video at which to start playing. Fast-forward, Play, Rewind, Stop and other buttons resembling those of a video recorder are also provided below the "Timeline" slider 21. Slider controls for Brightness, Contrast, Saturation and Hue allow a user to adjust the video image.

Note that the exemplary video image shown in FIG. 2 as being played back is an infrared image of a subject's face (22). Different colors in the image represent different temperatures of portions of the subject's face. A spectrum of selected colors can represent a corresponding range of temperatures. Thus, as a reviewer or other user observes a portion of the image change from one color to another (or stay the same color), the reviewer can assess whether the subject is experiencing increasing stress, decreasing stress, or the same level of stress.

The GUI also includes an audio waveform graphic 23 that represents the audio signal. The user can view the graphic while listening to the recorded audio. The recorded audio is synchronized with the recorded video, and adjusting the Timeline slider changes the playback point in both the recorded audio and video.

Figure 3:
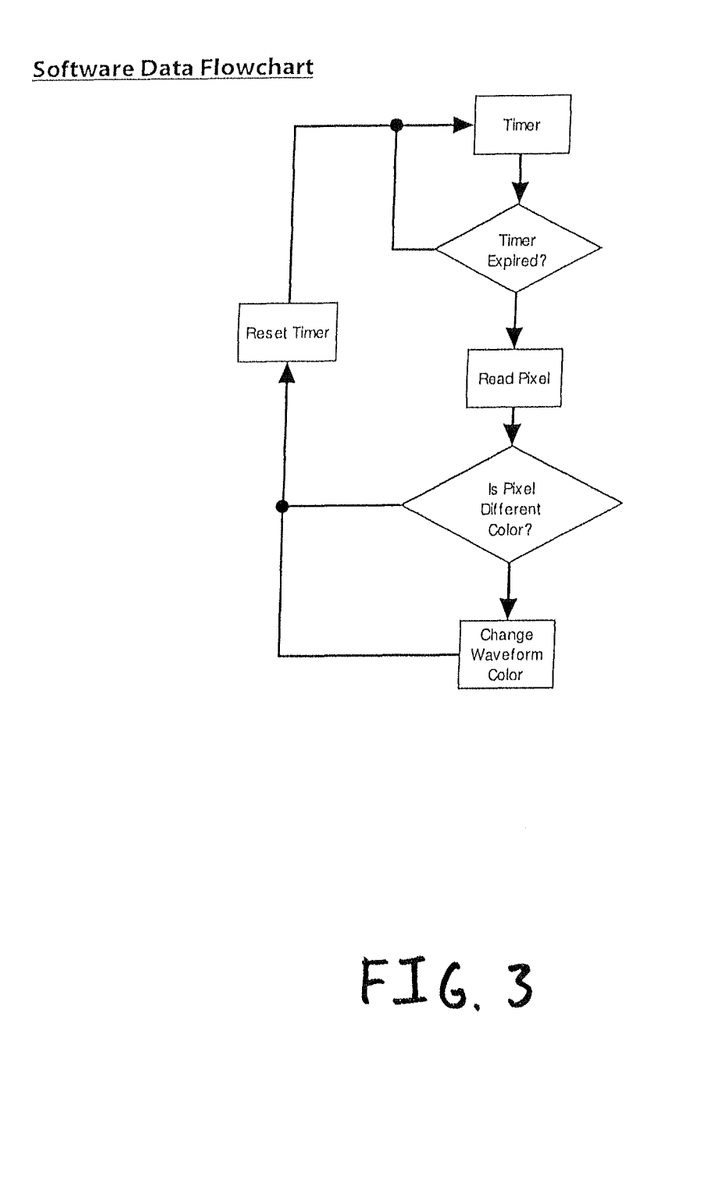
FIG. 3 is a flow diagram illustrating a method for setting the color of a voice waveform shown in FIG. 2 to reflect a measured stress level.

A "Color Track" checkbox 24 in the playback module or window allows the user to turn on and off a feature that causes the color of the audio waveform to track the color of a predetermined pixel in the image playback window 22, such as the center pixel. If the subject's face is centered in the camera image, the center pixel will represent a temperature of the person's face and thus, a measure of the stress experienced by the subject. Note that as the user moves the Timeline slider, the color of the audio waveform changes to reflect the relative stress level of the subject at the corresponding point in the interview. The flowchart of FIG. 3 illustrates an exemplary method for causing the audio waveform color to track the image pixel color.

Figure 4:
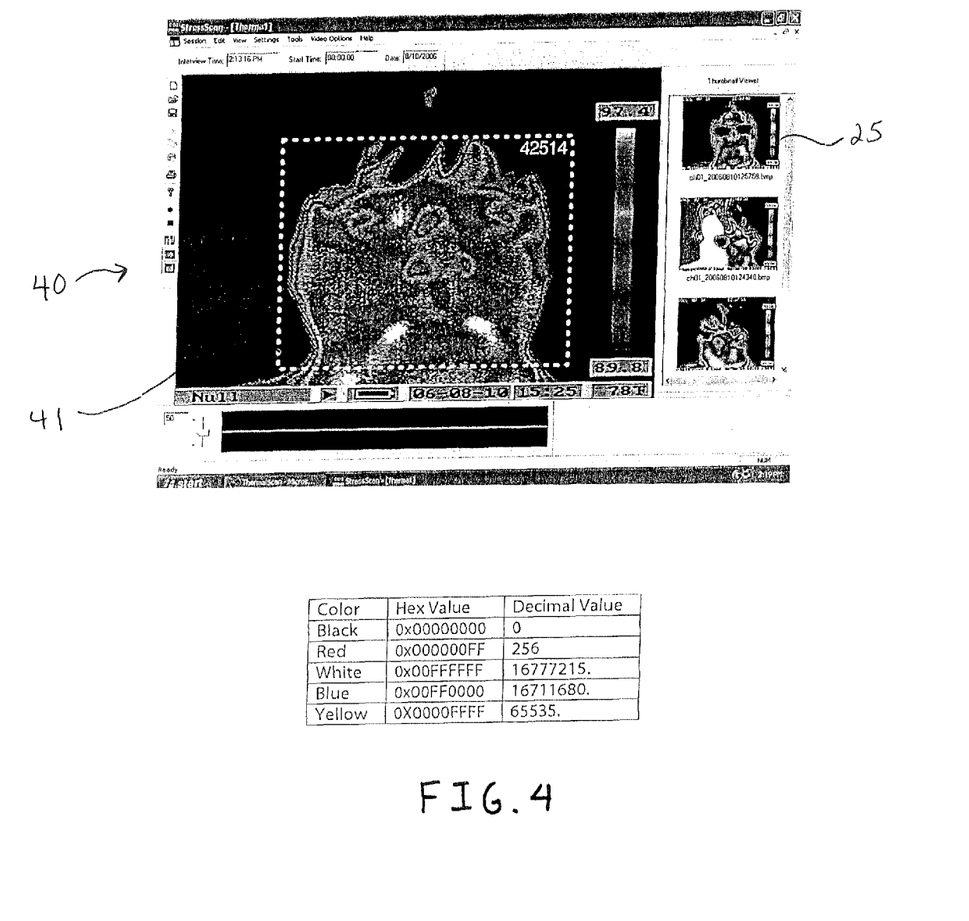
FIG. 4 depicts another exemplary screen display generated by computer software operating on the computer of FIG. 1.
Figure 5:
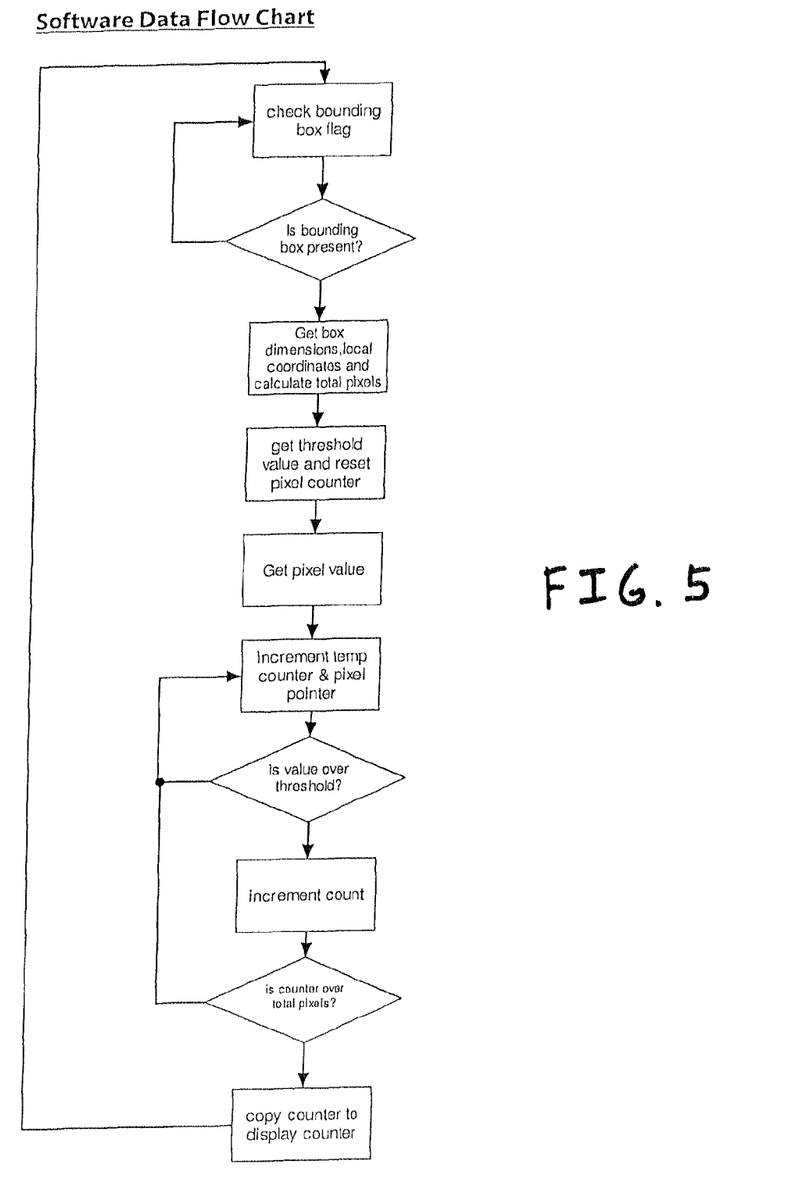
FIG. 5 is a flow diagram illustration a method for setting a stress value indicator shown in FIG. 4 to reflect a measured stress level.

As illustrated in FIG. 4, the GUI also provides a screen 40 that displays a numeric count of the number of pixels that exceed a predetermined color threshold in the spectrum and thus provides a numeric representation of the stress experienced by the subject. The GUI allows a user to draw (e.g., using a mouse or other input device) a bounding box 41 around a desired area in the image. The user can do this during the interview itself. Once the box is drawn, the number of pixels (e.g., 42,514 in FIG. 4) within the box that exceed the predetermined threshold is displayed. The flowchart of FIG. 5 illustrates an exemplary method for computing and displaying this number.

As shown in the right hand side of FIGS. 2 and 4, the GUI also allows the user to select and display thumbnail views or snapshots 25 taken during the interview or saved during review of recorded video.

The computer system can transmit the captured video and audio data streams to remote recipients or store them (e.g., on disk storage). To facilitate transmitting the video and audio data on a communication bus or other communication medium, the computer system, under control of a suitable software feature, can combine the multiple video and audio signals from the various cameras and microphones in an interleaved manner into a single data stream. The term "interleave" as used herein refers to combining two or more data streams in a time-division sequence arranged according to a specified set of rules such as alphabetically, numerically, or chronologically, resulting in a single data stream. "De-interleaving" refers to the segmentation and separation of a data stream according to a specified set of rules such as alphabetically, numerically, or chronologically resulting in multiple data streams. The computer system can de-interleave data streams that it receives or retrieves from storage so that the information can be viewed on the computer screen by an examiner as described above.

The computing systems described herein can store interview data (i.e., audio and video), which can ultimately be copied on a recording medium (e.g., a compact disc). The data can be viewed on other computers such as PCs with analysis software installed on the computer. The analysis software allows the investigator to open and analyze the interview data for further review. It is software that can be installed remotely, usually at the interviewers desk PC, that will allow the investigator to review previously collected interview data and perform functions such as playback of audio, playback of video, and book-marking certain parts of the interview, thereby enabling the investigator to piece together crucial elements of the interview. The software permits subsequent review of interview data, which can assist in future interviews. The analysis software is similar to the software tools available in the StressScan™ software, with the exception that analysis software does not receive video or thermal images like that of the StressScan™ software. The analysis software also includes the graphical user interface (GUI) software described above.

The devices described herein have numerous applications that involve the detection of stress. The devices and methods can have applications in several areas including, but not limited to, criminology, homeland security, personnel evaluation, psychiatry, clinical psychology, and self-testing for psychological behavioral assessment and feedback.

For example, the devices and methods can be used in psychiatry to evaluate levels of depression, alcoholism, drug addiction, and dementia. In addition, the devices and methods described herein can be used to assess and manage phobias.

In psychological testing, the devices and methods described herein can be used to assess the responsiveness to specific kinds of mental stress, which could be important in testing of students with psychological learning disabilities, as well as of employees or potential employees for their ability to cope with stressful tasks. The identification of particular learning or work situations that are excessively stressful can be key to improving the performance of students or employees.

The devices described herein can be used to improve the training of sales personnel, negotiators, teachers or orators, all of whom must cope with mental stress. It could also measure a variety of psychological parameters, such as the types of mental tasks that the subject finds more difficult or more enjoyable. These may include reading, calculating, solving different types of problems, listening to different kinds of music, different types of jokes, different kinds of visual sceneries, etc. In such psychological applications, like in the first part of a learning disability test, the goal of the test is to identify the type of mental stimulus that evokes a change in autonomic thermoregulation larger than a given threshold.

In one aspect, the source of stress is derived from an interrogating agency such as, for example, a police interrogation. The use of lie detection devices during police interrogations has been established for some time. For example, polygraph devices have been successful in the detection of truthfulness of the suspect; however, the polygraph is not always reliable. Furthermore, the polygraph requires a cooperative test subject who agrees to be connected to the device. The subject thus has knowledge that he or she is being tested to determine statement truthfulness. This can ultimately call into question the results of the polygraph test. The devices described herein are non-invasive, which means that the device is not in physical contact with the subject. However, it is contemplated that the devices described herein can be used along with other invasive techniques for detecting stress such as, for example, polygraph devices or devices known in the art for detecting blood flow in the subject, measuring the respiratory rate of the subject, or detecting perspiration.

In one aspect, when it is desirable to elicit and detect changes in stress level in a subject, the method comprises:
a. providing facts to the subject that will increase or decrease the level of stress of the subject;
b. requesting the subject to describe an event and detecting changes in the level of stress of the subject;

c. requesting the subject to provide additional details regarding sections or portions of information provided by the subject in step (b) and detecting changes in the level of stress of the subject; and d. requesting the subject to respond to questions comprising information only known to the subject and detecting changes in the level of stress of the subject.

Although the stress detection devices described herein can be used in this aspect, any techniques or devices for detecting stress can be used in this questioning methodology. For example, thermal imagers, video cameras, and devices for detecting changes in audio amplitude and frequency can be used alone or in any combination to detect changes in stress using the questioning techniques.

The first part of the questioning methodology involves revealing facts to the subject that are specifically designed to increase stress in an untruthful, involved, or guilty subject and to calm (i.e., reduce stress) in a truthful, innocent, or uninvolved subject. Next the subject is asked to describe an event or give an account of an incident. The subject is then requested to provide more detailed information regarding certain portions of their story. Additional requests for more details are made regarding interrelated portions of their statement. Under these conditions, an honest person should generally exhibit little change in stress as they are simply recalling the truth, while an untruthful suspect must remember all previous fabrications to keep their story consistent. The untruthful suspect will generally show significant and detectable signs of stress due to the fear of making conflicting statements. Finally, the subject is asked multiple-choice type questions or provided multiple scenarios that contain information only the subject would know about, and the levels of stress are detected. Ultimately, the questioning techniques will steadily increase levels of stress in a dishonest subject that can be readily detected and provide a reliable indicator of whether or not the subject is being dishonest.

As discussed above, an infrared camera is positioned so that it can measure changes in skin temperature of the subject. The infrared camera can be pointed to any exposed skin of the subject, with the neck, face, or combination thereof as the preferred areas. One or more visible light video cameras can be focused on the subject as well. A microphone is positioned in front of the subject as well. The interrogator begins to ask the subject questions during which time video and audio input data is generated and forwarded to an audio/visual room that has a computing system and monitor. The audio and video data is converted to visual data that can be displayed on the monitor for the examiner's review. The examiner can review concurrently changes in skin temperature and voice frequency/amplitude as well as monitor the subject's movements. If there is a noticeable change in skin temperature, voice frequency/amplitude, and/or movement/behavior of the subject, the examiner can notify the interrogator that a certain line of questioning is creating more stress in the subject with the use of a feedback system. The feedback system is a way the examiner can provide comments to the interrogator regarding output produced by the stress detection device. This can be useful in aiding the interrogator on where to focus the line of questioning. For example, the examiner can notify the interrogator by a flashing light system, (e.g., green light is little to no stress or red light is an indication of stress). In other aspects, a variable rate indicator can be used to provide feedback to the interrogator. Alternatively, the interrogator can have an earpiece or PDA (e.g., remote or wireless access) that is not obvious to the subject so that the examiner can be in direct communication with the interrogator.

In certain aspects, the stress detection system is equipped with a covert signaling device designed to facilitate the transmission of signals from the system operator in the monitoring room to the interviewer in the interview room. The signaling device will provide a means to send coded messages to the interviewer regarding observed changes in stress of the interview subject without the subject being aware of this communication. For example, colored lights, digital displays, and other signaling devices that are concealed in the interview room or other setting and not obvious to the subject can be used by the examiner to communicate with the interviewer.

Any of the components of the stress detection devices described herein (e.g., infrared cameras, video cameras, microphones, etc.) can be concealed so that the subject is not aware of the stress detection device. For example, the infrared camera can be concealed within a number of different substrates including, but not limited to, a standard sheetrock-stud constructed wall, a standard concrete block constructed wall, a 3-ring binder, computer hardware, behind wall art, or within interior fixtures, artifacts, and decorations. With respect to the lens opening for the infrared camera, the lens will be concealed using a short-wave, mid-wave, or long-wave infrared transparent material designed such that the lens blends into the installation setting such that the camera is inconspicuous to the subject.

The stress detection devices can produce real-time visual displays for detecting stress. However, it is contemplated that the visual displays can be stored for future use and review. In certain aspects, if a certain skin temperature is reached, the examiner will manually take one or more snapshots of the subject (e.g., skin temperature, audio frequency/amplitude) for future review. Here, the skin temperature of the subject can "trigger" the examiner to take a snapshot. In the alternative, the device can be configured so that snapshots of the subject are taken at specified time intervals. The snapshots are useful for comparing the subjects stress levels over certain periods of time during questioning. If desired, the snapshots can be displayed in the monitor so that they can be viewed concurrently while viewing thermal, video, and audio images generated by the subject. The "snapshots" are also referred to as a thumb-nail. When thumb-nails are used, the examiner can scan the monitor and pick out the thermal spikes, then review the corresponding video at a particular time stamp and refer back to the audio at the same point in time and listen to the conversation that generated the thermal spike. It is also contemplated that the thermal, video, and audio images generated by the device can be viewed simultaneously on one display device or, in the alternative, any combination of thermal, video, and audio images can be displayed.

The devices and methods described herein provide advantages over previous techniques. With respect to the audio and video data, the devices described herein provide a reference point between audio output data and the video output data. This is important with respect to correlating the audio data with the thermal and video data. The devices described herein use more than just a microphone in combination with the thermal imager and video camera. The audio data produced by the subject is converted to a graphical display of frequency and amplitude so that a change in audio frequency and amplitude can be correlated with a change in skin temperature and/or body movements of the subject. In other words, the audio information can be displayed in the time or frequency domain allowing visual comparison to the thermal and video data being generated during the interview. This feature is not appreciated by the art and provides a more reliable way to detect stress in a subject.

Throughout this application, various publications are referenced. The disclosures of these publications in their entireties are hereby incorporated by reference into this application in order to more fully describe the compounds, compositions and methods described herein.

Various modifications and variations can be made to the materials, methods, and articles described herein. Other aspects of the devices and methods described herein will be apparent from consideration of the specification and practice of the materials, methods, and articles disclosed herein. It is intended that the specification and examples be considered as exemplary.

What is claimed is:

1. A method for detecting stress in a subject, said method comprising:

said subject having a periorbital region;

optimizing the subject's temperature range to resolve only temperatures outside said periorbital region;

identifying a limited temperature range to establish a baseline for thermal values tailored to the subject to enable visualization of thermal changes in the subject;

establishing thermal thresholds based on said baseline;

displaying breaches outside said thresholds;

displaying the temperature values of said breaches;

adjusting said limited temperature range based on the unique temperature characteristics of the subject;

displaying a spectrum of different colors corresponding respectively to specific narrow temperature variations in regions selected from the cheeks, ears, forehead and neck or a combination thereof;

displaying selected color variations based on an audio waveform of the subject;

displaying the color spectrum of a predetermined pixel in an infrared video display;

varying a timeline of the combined audio waveform and infrared video image;

comparing the colors of the audio waveform and the infrared video image of said pixel at a particular point in time; and changing the audio waveform color to track the color variations of said pixel infrared video image.

2. The method claimed in claim 1, further comprising the step of providing a graphical user interface with a timeline control with which a user can select a point in a captured image to begin playing.

3. The method claimed in claim 1, further comprising the step of recording captured infrared and visible-light video images on a data storage medium.

4. The method claimed in claim 1, further comprising the step of receiving an audio signal from a microphone and playing the audio through a speaker.

5. The method claimed in claim 4, further comprising the step of displaying a graphical representation of the audio waveform in response to the audio signal.

6. The method claimed in claim 5, wherein said infrared video display comprises a center pixel and said method further comprising the step of displaying the graphical representation of the audio waveform in a color responsive to said center pixel of the displayed infrared video image.

7. The method claimed in claim 1, further comprising the step of interleaving data elements relating to a plurality of video images to form an interleaved data stream.

* * * * *